United States Patent [19]

D'Orazio et al.

[11] Patent Number: 5,773,270
[45] Date of Patent: Jun. 30, 1998

[54] THREE-LAYERED MEMBRANE FOR USE IN AN ELECTROCHEMICAL SENSOR SYSTEM

[75] Inventors: Paul A. D'Orazio, Mendon; David Sogin, Needham, both of Mass.

[73] Assignee: Chiron Diagnostics Corporation, E. Walpole, Mass.

[21] Appl. No.: 245,194

[22] Filed: May 17, 1994

Related U.S. Application Data

[63] Continuation of Ser. No. 667,831, Mar. 12, 1991, abandoned.

[51] Int. Cl.⁶ .............................. C12N 11/02; C12N 11/04; C12Q 1/54; C12M 1/40
[52] U.S. Cl. .............................. 435/177; 435/14; 435/25; 435/27; 435/179; 435/180; 435/182; 435/288; 435/817; 204/403
[58] Field of Search .................................. 435/177, 179, 435/180, 288, 817, 14, 25, 27; 204/403

[56] References Cited

U.S. PATENT DOCUMENTS

| | | | |
|---|---|---|---|
| 3,539,455 | 11/1970 | Clark, Jr. | 204/1 |
| 3,623,960 | 11/1971 | Williams | 204/1 T |
| 3,770,607 | 11/1973 | Williams | 204/195 |
| 3,979,274 | 9/1976 | Newman | 204/195 |
| 4,073,713 | 2/1978 | Newman | 204/195 |
| 4,220,503 | 9/1980 | Johnson | 204/1 T |
| 4,240,438 | 12/1980 | Updike et al. | 128/635 |
| 4,240,889 | 12/1980 | Yoda et al. | 204/195 |
| 4,260,680 | 4/1981 | Muramatsu et al. | 435/14 |
| 4,340,448 | 7/1982 | Schiller et al. | 204/1 T |
| 4,340,458 | 7/1982 | Lerner et al. | 204/195 |
| 4,353,983 | 10/1982 | Siddigi | 435/11 |
| 4,356,074 | 10/1982 | Johnson | 204/195 |
| 4,388,166 | 6/1983 | Suzuki et al. | 204/403 |
| 4,392,933 | 7/1983 | Nakamura et al. | 204/403 |
| 4,404,066 | 9/1983 | Johnson | 204/1 T |
| 4,415,666 | 11/1983 | D'Orazio et al. | 435/179 |
| 4,418,148 | 11/1983 | Oberhardt | 435/179 |
| 4,440,175 | 4/1984 | Wilkins | 128/635 |
| 4,442,841 | 4/1984 | Uehara et al. | 128/635 |
| 4,671,288 | 6/1987 | Gough | 128/635 |
| 4,679,562 | 7/1987 | Luksha | 128/635 |
| 4,750,496 | 6/1988 | Reinhart et al. | 128/635 |
| 4,759,828 | 7/1988 | Young et al. | 204/1 T |
| 4,795,707 | 1/1989 | Niiyama et al. | 435/288 |
| 4,820,399 | 4/1989 | Senda et al. | 204/403 |

*Primary Examiner*—David M. Naff
*Attorney, Agent, or Firm*—Arthur S. Morgenstern; Gerry A. Blodgett; Robert P. Blackburn

[57] ABSTRACT

A system for electrochemical measurement of glucose concentration in an undiluted test sample, e.g. blood is provided containing a sensor including a three-layered contiguous membrane. The membrane has a thickness of 50 to 130 microns, and is composed of a 1 to 10 micron thick first layer, a 10 to 30 micron thick second layer having an average pore diameter of 15 nanometers and a 40 to 80 micron thick third layer containing glucose oxidase. The third layer is less dense than the first and second layers and the first layer is more dense than the second layer. The layers of the membrane are fused together such that no clear distinction can be made between the layers at the boundary. The sensor is calibrated in a standard glucose solution which includes catalase as a hydrogen peroxide scavenger, and the sensor has a response that is linear throughout the concentration range of glucose in an undiluted sample. In one embodiment, the system is a polarographic cell structure containing an electrically insulating receptacle, an electrode mounted in the receptacle, and the three-layered membrane.

15 Claims, 1 Drawing Sheet

THREE-LAYERED MEMBRANE FOR USE IN AN ELECTROCHEMICAL SENSOR SYSTEM

The application is a continuation of application Ser. No. 07/667,831, filed Mar. 12, 1991, now abandoned.

BACKGROUND OF THE INVENTION

The present invention relates to a sensor system for performing blood analyses, especially glucose concentration. The system includes a special calibration solution, a sensor, a membrane suitable for use with the sensor and a method of making said novel membrane. The membranes of this invention are used in voltametric cells for electrochemical analysis. Such cells are commonly referred to as polarographic cells and are so denominated hereinafter. These cells employ an enzyme for converting a substance which is not polarographically active into a polarographically active substance which can be measured by reading an electrical signal from the cell.

A wide variety of assay techniques and sensors are available for the measurement of various materials. Of particular interest to the medical field, is the measurement of small amounts of various substances contained in body fluids, such as blood, serum or plasma, spinal fluid, in body tissues, in foodstuffs, and the like. Such substances include glucose, urea, uric acid, triglycerides, phospholipids, creatinine, amino acids, lactic acid, xanthine, chondroitin, etc. The development of a sensor for controlling or monitoring the glucose concentration in blood or other body fluids is particularly important especially for maintaining normal blood glucose levels in a diabetic patient. Typically, blood samples are withdrawn from the patient for an on-line analysis for glucose concentrations using a glucose oxidase membrane with a polarographic detector (electrode) for the generated hydrogen peroxide. The sensor is intermittently calibrated using aqueous glucose solutions of known concentration. Customarily, such detectors comprise an enzyme electrode for the determination for hydrogen peroxide with an anode, a cathode, an electrolyte, and a membrane of specific composition containing an enzyme that has been immobilized.

Enzymes have been used in conjunction with polarographic cells in instances where the unknown substance to be measured is not electrochemically active itself, but by conversion or reaction of the enzyme with the unknown sample, a reaction product is obtained that may be measured; that is, it is detectable by a polarographic means. As stated above, one analysis of medical interest is the desire to measure blood glucose. In this measurement, it is advantageous to employ an enzyme to gain specificity. In the presence of the enzyme glucose oxidase the following reaction takes place:

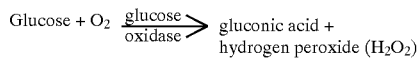

The hydrogen peroxide that is generated by this reaction is measurable by a polarographic detector and therefore, by appropriate calibration and calculations, it is possible to determine, from the amount of $H_2O_2$ liberated or from the rate of liberation what the glucose content was in the original specimen or test sample.

Generally, a polarographic cell comprises an electrically insulating receptacle, an indicator or sensing electrode electrically contacting a membrane and a reference electrode which is electrically in contact with the membrane. By the expression "contacting" it is intended to include the situation where the contact between membrane and electrode is obtained directly or through a layer of electrolyte. Cells of various designs are widely known and understood in the art. An especially suitable cell for purposes of the invention is shown in D'Orazio et al, U.S. Pat. No. 4,415,666.

TECHNICAL REVIEW

In the case of an enzyme membrane structure, it is known to arrange a second hydrophilic membrane at a distance from the first mentioned membrane. In the space between the two membranes a layer of concentrated enzyme is present. The free face of the second membrane provides the test surface to which the substrate to be tested is applied. This type of enzyme membrane is described in the Annals of the New York Academy of Science, Vol. 102 (1962). pages 29–49. In that article, it was suggested that a pH sensitive electrode could be used to detect gluconic acid produced by the reaction. It was disclosed that the enzyme in such a system could be trapped between two cellulose acetate membranes. Glucose diffuses through the membrane and is converted by the enzyme to gluconic acid which then diffuses both towards the pH sensitive glass and back into the sample solution.

The first mentioned membrane facing the sensing electrode is made up of a material which can be penetrated by the substance to which the sensing electrode is sensitive. For example, this membrane is permeable to the reactants and the products of the enzymatic reaction but impermeable to the enzyme itself. It may be of cuprophane, but, in the event that one of the reaction products is a gas at normal pressure and temperature and it is desired to measure via this gas, the membrane may consist of hydrophobic plastic impermeable to ions but slightly permeable to such gases as oxygen, carbon dioxide or ammonia. Numerous plastics having such properties are known including silicone rubber, tetrafluoroethylene and the like.

In a later type of polarographic cell developed by Clark and described in U.S. Pat. No. 3,539,455, the enzyme is placed on the electrode side of the membrane, and a platinum anode measures the hydrogen peroxide produced. Glucose, a low molecular weight species, passes through the membrane and reacts with the enzyme, but interfering high molecular weight substances such as catalase and peroxidase do not. It is disclosed that the enzymes may be held in a thin film directly between the platinum surface and the membrane by placing the enzyme on a porous film which has spaces large enough to hold enzyme molecules. However, cellophane membranes will not prevent low molecular weight interfering materials such as uric acid or ascorbic acid from reaching the sensing electrode. Clark suggests a dual electrode system to overcome that problem. The compensating electrode, without an enzyme present, gives a signal for the interfering substances while the enzyme electrode detects both the hydrogen peroxide and the interference. By appropriate calculation, the glucose level is determined. Such a dual sensor system, however, may encounter difficulties in the matching of the two cells.

It was then proposed to have an enzyme electrode which employs a thin filter membrane to prevent passage of low molecular weight interfering materials, e.g. uric acid and ascorbic acid, while permitting hydrogen peroxide to pass therethrough with minimum hindrance. Membrane materials exist, such as silicone rubber and cellulose acetate, which permit passage of hydrogen peroxide but which are effective barriers to interfering substances. Since this type of membrane must be placed between the sensing electrode and some component of the sensing system, it follows that, in order for measurement equilibrium to be as rapid as possible, the membrane must be as thin as possible while still retaining its selectivity. In the case of a hydrogen peroxide sensing probe, this membrane will need to be less than 2 microns thick. A membrane of this thickness is difficult to use in practice because of its insufficient strength.

The art then turned to depositing the material in a thin layer on a porous substructure to provide the necessary strength while at the same time being of little hindrance to hydrogen peroxide passage. The weak interference rejecting layer can be thin to enhance speed of response.

As described in Newman, U.S. Pat. No. 3,979,274, in a laminated two-ply membrane, an enzyme adhesive is used to bond the two-plies together. The membrane includes a support layer which controls substrate diffusion and serves as a barrier to high molecular weight substances, an enzyme preparation for reacting with the substance to be determined and for bonding the layers together, and an essentially homogeneous layer that serves as a barrier to interfering low molecular weight materials but permits hydrogen peroxide to pass through. However, in this development, it is necessary to make a sandwich consisting of two membranes with a layer of enzyme between, the enzyme acting as the adhesive or bonding agent. In this type of arrangement, the use of too much enzyme could slow down the diffusion of the diffusing species to an unacceptable amount. If a thinner layer of enzyme is used, there is acceptable diffusion, but the loading of enzyme may not be adequate.

A still later development came in British Pat. No. 1,442,303 wherein there was proposed a composite membrane which is an inhomogeneous membrane formed as a unit. The membrane has two different strata, one has a thickness of less than 5 microns and the other is sufficiently thick to provide strength. The enzyme is bonded to a surface of the membrane.

Other prior art have shown a number of disadvantages.

The method of Koyama et al., *Analytica Chemica Acta,* Vol. 116, pages 307–311 (1980), immobilizes glucose oxidase to a cellulose acetate membrane. This method is more time consuming; it involves more steps and suffers from the disadvantages that a monolayer of molecules would be the maximum possible enzyme load achievable.

The invention described in the present application, however, allows much greater amounts of enzyme to be spacially distributed within the membranes such that much more enzyme is available for reaction with the substrate along the diffusion path of said substrate.

Wingard et al., *The Journal of Biomedical Materials Research,* Vol. 13, pages 921–935 (1979) discloses a platinum screen or wire for immobilization of an enzyme. This might allow greater surface area to be utilized for binding than the method of Koyama et al. and hence could employ greater numbers of enzyme molecules. However, the approach of Wingard is also limited to a monolayer of enzyme and is capable of sustaining high conversion rates of substrate diffusing through the open spaces in the platinum screen only near the surface of the platinum wire. Hence, this prior art cannot achieve the theoretical conversion rates possible with an enzyme spacially distributed throughout a membrane through which the substrate diffuses, as is obtainable by following this invention.

CLARK (U.S. Pat. No. 3,539,455)

A polarographic device for measurement of polarographically inactive materials by means of an enzyme which converts the inactive material (such as glucose) to a polarographically active material such as hydrogen peroxide.

WILLIAMS (U.S. Pat. No. 3,623,960)

An electrochemical apparatus for measuring glucose concentration in a sample by employing a reaction between glucose, quinone, and oxygen, catalyzed by glucose oxidase.

WILLIAMS (U.S. Pat. No. 3,770,607)

The electrochemical apparatus described in Williams above, with additional discussion of the membrane including reference to a cellulose acetate membrane and to the notion of immobilizing the glucose oxidase in a porous membrane.

NEWMAN (U.S. Pat. No. 3,979,274)

A polarographic cell for detecting glucose concentration by detecting hydrogen peroxide concentration, after glucose oxidase reaction, in which the need for an interfering material compensating electrode is eliminated by a multi-layer membrane which excludes even low molecular weight interfering materials from the electrode. The layer (for example, of cellulose acetate) is of sufficiently small pore size to exclude ascorbic acid and uric acid. The sample side layer has larger pores and excludes high molecular weight material. An adhesive bond between the two layers includes the glucose oxidase.

NEWMAN (U.S. Pat. No. 4,073,713)

The polarographic device described in Newman (U.S. Pat. No. 3,979,274) in which the outer, large pore size membrane are discussed and in particular a perforated polycarbonate film having 0.03 micron pore size is disclosed.

JOHNSON (U.S. Pat. No. 4,220,503)

A process for stabilizing the activated form of galactose oxidase enzyme, particularly for use in membrane protected polarographic electrodes.

UPDIKE (U.S. Pat. No. 4,240,438)

A sensor for measuring glucose concentration in a blood sample in which the electrode is protected by a hydrophobic membrane in which are embedded glucose oxidase. The patent proposes that the only polarographically active element which reaches the electrode is oxygen since it is the only material which can pass through the membrane.

YODA (U.S. Pat. No. 4,240,889)

A polarographic electrode for measuring glucose concentration in a sample, by measuring the hydrogen peroxide concentration on the electrode side of a membrane containing glucose oxidase. The membrane has a large pore layer on the sample side which allows glucose to reach the glucose oxidase immobilized in that layer. The electrode side of the layer is highly dense and only allows hydrogen peroxide to pass through to the electrode.

MURAMATSU (U.S. Pat. No. 4,260,680)

A polarographic electrode for determining the concentration of glucose in a sample in which the sample is pre-treated with an ion exchange compound to remove certain interfering compounds from the sample. Furthermore, the electrodes are driven by alternating square wave current rather than DC.

SCHILLER (U.S. Pat. No. 4,340,448)

A polarographic sensor for determining the concentration of glucose in a sample by monitoring the concentration of hydrogen peroxide at an electrode. The sensor is rendered more linear by placing both glucose oxidase enzyme and catalase enzyme in the vicinity of the electrode.

LERNER (U.S. Pat. No. 4,340,458)

A method of directly measuring the concentration of glucose in a blood sample by imposing a forward and backward voltage sweep on electrodes and integrating the current. The effect of interfering chemicals is reduced.

SIDDIQI (U.S. Pat. No. 4,353,983)

A sensor system for monitoring the concentration of glucose in a sample by producing hydrogen peroxide catalyzed by glucose oxidase, and then reacting the hydrogen peroxide with a fluorine compound to produce F—. The concentration of F— is actually monitored by the sensor.

JOHNSON (U.S. Pat. No. 4,356,074)

A polarographic cell for measuring the concentration of a non-polarographically active compound in a sample by converting the compound to a polarographically active compound using an enzyme held between two layers of a membrane. The specificity of the enzyme is controlled by controlling the oxidation reduction potential of the enzyme environment.

SUZUKI (U.S. Pat. No. 4,388,166)

A polarographic electrode for measuring the concentration of glucose in a sample having a multi-layer membrane separating the electrode from the sample. The inner layer of the membrane is highly porous and carries an enzyme for converting the glucose to a polarographically active compound. The outer layer of the membrane is a asymmetric semi-permeable membrane which excludes large compounds which tend to follow the electrode. It is noted that the presence of the outer layer also reduces noise in the system.

JOHNSON (U.S. Pat. No. 4,404,066)

A refinement of the electrode described in Johnson (U.S. Pat. No. 4,356,074) in which the oxidation reduction potential control mechanism over the specificity of the enzyme is accomplished using inner multi-layers of membrane within the multi-layers of the total membrane.

NAKAMURA (U.S. Pat. No. 4,392,933)

A solid state electrode for measuring the presence of hydrogen peroxide in a solution in which an oxidase is deposited on a metal oxide.

D'ORAZIO (U.S. Pat. No. 4,415,666)

A polarographic system for measuring the concentration of glucose in a sample in which the sample is separated from the electrode by a multi-layer membrane. The sample side layer is a thin relatively dense small pore layer which passes glucose but excludes such interfering substances as uric acid, ascorbic acid and other large non-gaseous molecules in similar substances. The electrode side layer is a highly porous membrane in which are immobilized the enzyme glucose oxidase. A middle layer formed of the highly porous material of the electrode side layer is present simply to separate the inner and outer layers but does not contain the enzyme. The finely porous outer layer specifically excludes catalase and peroxidase, as it has a cut off of a molecular weight of approximately 300.

WILKINS (U.S. Pat. No. 4,440,175)

A potentiometric or polarographic electrode system for measuring the concentration of glucose in a sample in which the electrode is coated with a membrane which contains an ion exchange compound and an insoluble salt of glucose.

UEHARA (U.S. Pat. No. 4,442,841)

A polarographic sensor for measuring the oxygen content in a sample in which the electrode is separated from the sample by a small pore membrane having an average pore diameter of 0.10 micron to 0.7 micron and an inner layer with a larger pore diameter. The multi-layers are selected to allow easy entrance of oxygen but to exclude blood cells.

TAKATA (U.S. Pat. No. 4,452,682)

An automated blood analysis system which includes as generally described a cell for monitoring glucose in the sample by reacting the glucose with glucose oxidase and then directly monitoring the resulting hydrogen peroxide.

GOUGH (U.S. Pat. No. 4,671,288)

A polarographic sensor located in the side of an invasive needle, for measuring the glucose concentration in body fluids. The sensor is separated from the body fluids by a membrane which restricts the diffusion of glucose while remaining relatively permeable to oxygen in order to avoid lack of oxygen as a rate controlling element of the sensor process.

LUKSHA (U.S. Pat. No. 4,679,562)

A sensor for determining the concentration of glucose in blood is designed around an iridium electrode with an oxidized surface upon which is bonded a layer of silane and then is bonded to the silane a layer of glucose oxidase. The structure is surrounded by a film of silicone rubber which is porous to glucose and oxygen.

REINHART (U.S. Pat. No. 4,750,496)

A polarographic sensor for detecting glucose present at the mucosal surface of a living being by monitoring glucose oxidase mediated conversion of glucose to peroxide, including a membrane separating the sample from the sensor. The membrane has three layers, the sample side layer is primarily protective, but is developed with pore size which excludes substances having a molecular weight greater than 3500. The central layer is porous and carries glucose oxidase, the inner layer is formed of cellulose acetate and has a pore structure which excludes molecules with molecular weight greater than 100. Therefore, little else than hydrogen peroxide will penetrate to the sensor electrode.

YOUNG (U.S. Pat. No. 4,759,828)

A polarographic sensor for determining the concentration of glucose in a sample in which a multi-layer membrane separates the sample from a hydrogen peroxide sensitive electrode. The sample side layer of the membrane has a thickness of 1 to 20 microns, preferably 5 to 7 microns and a pore size of 10 to 125 angstroms, which limits the diffusion of glucose molecules through the membrane and insures the presence of sufficient oxygen in contact with the immobilized enzyme. This is allegedly set up to avoid the problem of prior membranes that sometimes, particularly in the case of samples having high concentrations of glucose, the amount of glucose coming into contact with the immobilized enzyme exceeds the amount of oxygen available. Consequently, the oxygen concentration is the rate limiting component of the reaction rather than the glucose concentration. Thus, the accuracy of the sensor is destroyed. Between an inner and the outer layer is a layer of glucose oxidase formed of a mixture of the enzyme and a cross linking agent such as glutaraldehyde. The inner layer has a thickness of 2 to 4 microns and preferably 2 to 3 microns and provides sufficient permeability to insure rapid removal of hydrogen peroxide from the enzyme into contact with the sensor electrode and rapid achievement of an equilibrium state. The device claims to be linear to concentrations above 500 mg/dl. It appears that the device is measuring initial rate change and potential rather than equilibrium values of difference in potential.

NIIYAMA (U.S. Pat. No. 4,795,707)

A polarographic electrode for measuring the concentration of glucose in a sample by converting the glucose, by means of glucose oxidase in a membrane, into hydrogen peroxide which is measured directly. The membrane separates the sample from the working electrode. The membrane is constructed in three layers. The outer or sample side layer has the immobilized glucose oxidase as its major component. The middle layer is a porous membrane which selectively allows diffusion of hydrogen peroxide. The inner layer is a thin layer of the hydrogen peroxide decomposing enzyme catalase. The inner layer is positioned so that it does not functionally separate the working electrode from the middle porous layer. As a result, the path of the hydrogen peroxide which is generated by the outer layer is through the middle porous layer and to working electrode and then, outwardly from the working electrode to be eliminated by the catalase. The purpose of the catalase presence is to reduce the accumulation of hydrogen peroxide at the electrode over time particularly in a sensor for continuously monitoring a flowing stream of diluted sample, in which situation, the base line and therefore the calibration tend to elevate as the hydrogen peroxide accumulates within the sensor.

SENDA (U.S. Pat. No. 4,820,399)

A sensor system for measuring the concentration of glucose in a sample employing the principal of the enzyme electrode which directly measures the electric function of enzyme activity rather than measuring the products (such as hydrogen peroxide, as is employed by the more conventional oxygen electrode. In this system, the glucose oxidase is immobilized on a porous medium and with it is immobilized an electron transfer mediator such as nicotinamide adenine dinucleotide, which allows the electrode to directly monitor the catalytic activity.

CHURCHOUSE (1986)

Churchouse, S. J. et al. *BIOSENSORS*, 2, 325–342 (1986)

An amperometric cell for measuring glucose concentration in flowing blood employs a platinum-stainless steel electrode coated with three membrane layers. The inner layer is polyethersulphone and functions to reduce electro chemical interference with other electrolytes and to enhance linearity. The middle layer is formed of glucose oxidase, albumin, and glutaraldehyde. The outer layer is polyurethane and provides diffusion limitation.

JONES (Miles) (1986) EPO Patent Application 86108293.1

An electrochemical sensor for measuring glucose concentration includes a platinum anode on which is deposited an enzyme and then an outer layer of a specifically formulated, biocompatible, silicon-containing compound. The permeability of the outer layer for oxygen is very high, for glucose is high, and for interferants is very low. The sensor is linear over the glucose range of whole blood. The formation of the outer layer involves in-situ polymerization of an organosiloxane dispersion in a carrier.

GENSHAW (1988)

Genshaw, M. A. *CLIN. CHEM.*, 34, 1717–19 (1988)

A polarographic cell for determining glucose concentration in which glucose oxidase is bonded directly to a platinum anode and a thin layer of silicone rubber overcoats the enzyme. The silicone is selected to be more permeable to oxygen than to glucose, so that more oxygen than glucose reaches the enzyme. The sensor is linear for glucose over the clinical range of undiluted blood, when equilibrium sensor current (4 minutes) is measured.

VADGAMA, P. (1988)

Vadgama, P. (1988) 'Diffusion Limited Enzyme Electrodes: In': *ANALYTICAL USES OF IMMOBILIZED BIOLOGICAL COMPOUNDS FOR DETECTION, MEDICAL, AND INDUSTRIAL USES,* eds Guilbault G. G. and Mascini M., D. Reidel Publishing Co., 1988, p. 359–377

An enzyme electrode for measuring glucose concentration is provided with a porous polymeric covering membrane treated with organosilanes. The covering membrane is highly permeable to $O_2$ and allows the response to be linear up to 500 mmol/l. The cover membrane is formed of polycarbonate, or polyurethanes, or cuprophan, and silanised to reduce fouling by blood components. The sensor has an inner membrane that passes only small molecules ($H_2O_2$) thereby eliminating interferants, a middle enzyme layer, and the cover layer which extends linearity.

YAMASAKI (1989)

Yamasaki, Y. et al., *CLINICA CHIMICA ACTA,* 93 93–98. (1989)

A needle-type sensor for measuring glucose in whole blood is highly linear to 800 mg/dl. and exhibits reduced fouling by blood components. The platinum anode of the hydrogen peroxide electrode is coated with an inner membrane of cellulose diacetate, into which a layer is absorbed of glucose oxidase. Then, a semi-permeable polyurethane membrane is deposited which freely passes oxygen but reduces glucose diffusion to linearize sensor response. Finally, a blood compatability membrane is deposited in three sublayers: alginate, polylysine, alginate.

SUMMARY OF THE INVENTION

In accordance with the present invention, the need to prepare a discrete enzyme layer is eliminated by incorporating the enzyme directly into one portion of the membrane in a manner whereby the enzyme is homogeneously dispersed throughout the phase of the membrane and immobilized therein.

A number of advantages characterize the present invention including ease of preparation, the permanent attachment of the phases of the membrane with no chance of separation; i.e., avoidance of lamination. Also the new membrane readily lends itself to a dip casting process whereby the membrane can be fixed directly to a miniature electrode, or to a base with electrical contacts.

In addition, a greater uniformity of enzyme concentration may be achieved by the homogeneous distribution in a membrane than by sandwiching bulk enzyme between two layers.

The principles involved in the present invention may be more fully understood with reference to the analysis of blood for glucose content. The liquid components of blood consists of proteins, lipids, and other substances. Nonelectrolytes are present, such as glucose, enzymes such as catalase, electrolytes such as ascorbic acid (vitamin C) and various metallic salts made up of cations of sodium, potassium, magnesium, calcium, iron and copper, and anions such as chlorides, phosphates, bicarbonates, and carbonates. The phosphates, carbonates and bicarbonates operate as buffers to maintain the pH of blood at a fixed level under normal conditions. If a sample of whole blood were placed on one side of a membrane and an aqueous solution of the enzyme glucose oxidase and oxygen is on the other side of the membrane, certain low molecular weight components will pass from the whole blood through the membrane to the glucose oxidase solution. The high molecular weight components such as the enzymes, and cells and cellular materials will not pass through the membrane. The rates of permeability of the various liquid components through the membrane are fixed because of the nature of the membrane. In this invention, the relatively thin phase has a molecular cut off of approximately 300 daltons or less. This means that components of a molecular weight of greater than about 300 daltons will not pass through.

Glucose, a low molecular weight component, will pass through the membrane and react with the enzyme glucose oxidase in the presence of oxygen to form gluconolactone and hydrogen peroxide. Gluconolactone in the presence of water will hydrolyze spontaneously to form gluconic acid.

Gluconic acid and hydrogen peroxide, being relatively low molecular weight materials compared to the enzyme glucose oxidase, will pass through the membrane, in both directions. Catalase and peroxidases, which are large enzyme molecules capable of rapidly destroying $H_2O_2$ and which are present in biochemical fluids, are prevented from passing, from the sample, through the membrane.

According to the present invention, the membrane may be utilized in a cell for electrochemical analysis comprising, in general, an electrically insulating receptacle, an anode and a cathode as is shown in U.S. Pat. No. 4,415,666. The membrane of this invention may also be used in older type devices utilizing a sensing electrode (anode), a reference electrode (cathode) in a space in the receptacle which is separated from the sensing electrode and adapted to hold an electrolyte. The membrane electrically contacts the electrodes; a path for an electrical current extends between anode and cathode or between the reference electrode and the sensing electrode and the membrane comprising the multi-component, integrated enzyme membrane which is described herein.

One portion of the membrane of the invention has a relatively high density and is relatively thin, the middle layer has a relatively lower density and is thicker, and the third portion of the membrane has the lowest density and the thickest cross-section. The portion of the membrane which has the thickest cross-section has the enzyme incorporated and immobilized therein and distributed homogeneously throughout.

It is a characteristic feature of the preferred embodiment of the present invention that the composite membrane is formed in three distinct steps and has different strata or portions parallel to the surface of the membrane. It is desired to provide another layer, substantially without enzyme, between the inner and outer layers. The use of a second phase inversion layer (without enzyme), with very small pore size, between the dense layer and the phase inversion enzyme layer appears to allow a better membrane to be manufactured by providing more linear response characteristics in undiluted test samples. More specifically, it proportionally reduces glucose diffusion, relative to oxygen diffusion, so that excess oxygen at the enzyme is maintained. This keeps oxygen concentration from controlling the reaction and making the reaction rate nonlinear at high glucose concentrations. The multilayer membrane blocks the migration to the sensing electrode of interfering substances such as uric acid, ascorbic acid, and large nongaseous molecules and similar substances and allows the passing of solvent and low molecular weight species, for example, enzymatic conversion products such as hydrogen peroxide.

A membrane exhibiting these properties can be made of cellulose acetate as well as other materials such as copolymers of cellulose acetate and of silicone.

It has been determined that a reasonably short measuring time requires that the thickness of the membrane should not exceed, preferably, about 90 microns although this can vary depending on the kind of measurement to be carried out. It would be possible to achieve an acceptable short response time for hydrogen peroxide, by designing the membrane to be made up of the thinnest, most dense layer of 2 to 5 microns, a thicker, less dense layer of 20 microns, and the thickest, least dense layer of about 65 microns.

The weaknesses inherent in the prior art have been overcome by forming the composite membrane according to the novel method of the invention. It consists, preferably, of three phases which are not necessarily distinct, but which, when cast separately and independently of each other, are characterized as: a highly porous, relatively thick phase which in the composite membrane faces the electrodes, a relatively nonporous, very dense and thinner phase which, in the composite membrane, faces the sample; e.g., the blood specimen, and a relatively dense middle layer which resists the diffusion of glucose but not of oxygen. In the composite membrane, the porosities and thicknesses of the three membranes may become modified as they are fused together. There is uniformly distributed throughout the highly porous phase, a particular enzyme. This enzyme may, however, become distributed throughout the composite membrane. Since an intermingling or diffusion of the layers is believed to occur, the terms layers and phases are used interchangeably to mean layers which may interact at their interfaces.

The individual properties of the phases forming the composite membrane, if cast separately should be as follows: the relatively nonporous phase should, if cast by itself and tested, have a molecular weight cut off of approximately 300 daltons; the highly porous phase, if cast by itself and tested, should freely pass the reactants for the enzyme (at the surface adjacent to the surface onto which it has been cast) and yet exclude macromolecules such as large proteins, and a middle layer which has an average pore size of 15 nanometers and which exhibits relatively high diffusion resistance to glucose but relatively low diffusion resistance to oxygen.

In order to achieve the desired properties for detection of an analyte, the membrane of the invention is preferably fabricated in a three stage process. First, an ultra thin cellulose acetate membrane is cast or spread on a suitable surface which does not interact with or bond to the membrane. Representative surfaces to provide a support for the cast film are glass and some plastics such as polyethylene. The film is cast with conventional equipment whereby it is possible to control the thickness of the resulting film. After being spread on the surface, the cast film is dried. This thin film serves as the relatively nonporous thin phase. The thickness of this phase generally ranges from about 1 to 10 microns, preferably from 2 to 5 microns. The glucose resistance layer of cellulose acetate membrane is then cast directly on top of the ultra thin membrane. Since both casting solutions are of the same polymer base, and preferably use the same solvent, there is a diffusion zone of the two at the interface or boundary and no clear distinction can be made between the two phases.

A thicker phase inversion type of cellulose acetate membrane containing the enzyme is then cast directly on top of the glucose resistance layer. Since both casting solutions are of the same polymer base, and preferably use the same solvent, there is a diffusion zone of the two at the interface or boundary and no clear distinction can be made between the two phases.

The order of casting may also be reversed, although it is preferred to cast the thin film first. The films may be allowed to dry under ambient conditions, or a heating device may be utilized. The first film need not be absolutely dry when the next film is cast on it; i.e., the first film may be tacky to the touch. It is believed that a skin forms on the top surface of the thick film after drying.

The solution of cellulose acetate used for the formation of the thin, more dense membrane component is formed by dissolving a cellulose acetate polymer in an inert organic solvent such as a ketone. Typical ketones are acetone, cyclohexanone, methylethylketone and the like. Mixtures of miscible solvents may also be used. Concentration of the polymer in solvent may vary, as from 1 to 5%, preferably 2 to 3%. The film is cast with any suitable film applicator such as will produce a final product film thickness of 1–10 microns, preferably 2–5 microns in thickness.

The glucose resistance layer, that is, the thicker middle layer which reduces the diffusion rate of glucose from the sample to the enzyme layer, without reducing oxygen diffusion, is prepared by forming a cellulose acetate solution in an inert solvent such as a ketone. A nonsolvent or nonsolvent mixture for cellulose acetate such as ethanol is then mixed with the cellulose acetate solvent solution. The particular nonsolvent, e.g. ethanol, is not critical and others may be used. Lower chain alcohols are preferred. The important aspect is that the composition is chosen so that the pore size and thickness of the resulting membrane provides significant resistance to diffusion of aqueous glucose, but does not effectively resist oxygen diffusion.

The phase inversion member; that is the relatively porous thickest portion of the composite membrane of this invention, is prepared by forming a cellulose acetate polymer in solution in an inert organic solvent such as a ketone. A nonsolvent or nonsolvent mixture for the cellulose acetate such as an ethanol and water mixture is then mixed with the cellulose acetate solvent solution. The particular nonsolvent, e.g. ethanol, is not critical and others may be used. Lower chain alcohols mixed with water are usually preferred for this purpose. An aqueous enzyme solution is included as part of the nonsolvent phase. The enzyme, e.g., glucose oxidase, is usually employed in an aqueous solution containing from 500 to 5000 International units of the enzyme per ml. of water, although this can vary as will be apparent to those skilled in the art. Typical electrochemical sensors which can be employed with the membrane of this invention include the glucose electrode shown in U.S. Pat. No. 4,092,233.

The overall thickness of the membrane of the invention can vary from about 50 to about 130 microns, but is preferably approximately 90 microns. The thinner, more dense layer ranges from about 1 to 10 microns, preferably 2 to about 5 microns, the middle layer ranges from 10 to 30 microns, preferably 15–25 microns, and the thicker, less dense ranges from about 40–80 microns. Some variation in these values is permissible within the contemplation of this invention. The preferred membrane is about 90 microns in thickness, with one layer about 2 microns, the middle layer 23 microns, and another layer about 65 microns in thickness.

The linearity of the sensor of the present invention can also be accomplished by separating the enzyme from the sample with an ultra thin silicone membrane. This membrane would be coated on the sample side of the enzyme-bearing membrane. It would be designed to attenuate the diffusion of the compound, e.g., glucose, without unduly restricting the diffusion of oxygen.

The nature of the sensors of the present invention requires that they be calibrated frequently in order to establish the value of the sensor signal associated with each concentration of the compound. In this regard, one important anomaly existed in the prior art. When the prior art sensors were used to measure the glucose concentration of a sample of blood or blood plasma or serum and of an aqueous glucose solution, both of the same glucose concentration, the sensor readings varied greatly. The discrepancy could be minimized by diluting the sample and solution. A dilution of 1 to 10 proved satisfactory. There are circumstances where this resolution of the problem is not acceptable, for example, in vivo measurement.

The present inventor has discovered that the discrepancy between sensor measurement of the sample and the calibrating solution can be eliminated by including, in the calibrating solution, a hydrogen peroxide scavenger, such as catalase. Catalase is normally present in blood and, to a lesser extent, in plasma. It appears that its presence in undiluted blood or plasma alters the reading which this type of sensor would produce. By placing into the calibrating sample, a quantity of catalase equivalent to that which would be effectively present in the blood or plasma to be measured, the effect of the catalase can be compensated for.

BRIEF DESCRIPTION OF THE DRAWINGS

The following drawings illustrate the invention in further detail and the invention will be more fully understood by reference to these drawings wherein.

DESCRIPTION OF THE PREFERRED EMBODIMENT

Figure 1:
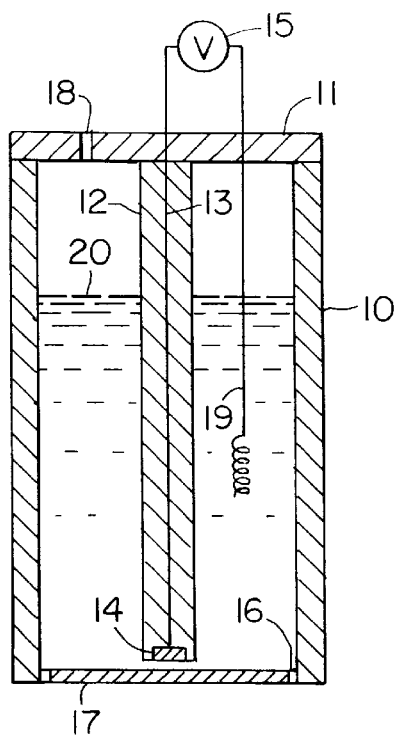
FIG. 1 is a vertical section view (partial) of a conventional polarographic cell utilizing the membrane of the present invention.

Referring to FIG. 1, there is shown a polarographic cell assembly which includes a receptacle in the form of an electrically insulating container 10 made of a plastic or glass material or any other suitable material and which may be of any cross-sectional area and shape, but is preferably cylindrical. This is covered by an electrically insulating cap 11. Positioned within the receptacle is an electrically insulating member rod, or cylindrical column 12, which contains in it an electrical conductor 13. This conductor is connected to an active or exposed element 14 which may be platinum, gold, silver, graphite or the like.

A lead is attached to the electrode which passes through the rod or column and through the cap to be connected with a D.C. voltage source 15. It is understood that alternative configurations of the cell assembly may be utilized in the practice of the present invention. One such alternate configuration may be a planar-type polargraphic cell.

The lower end of the receptacle is provided with a support means 16 such as a ring or retainer and the membrane 17 in accordance with the present invention is supported over the end of the supporting receptacle nearest the central electrode and spaced a capillary distance from the active face of the electrode. The membrane can be held in position with any suitable means, for example, by an O-ring fitting into a circular groove or other convenient means in the receptacle. A current measuring instrument 15 is connected in series with the cell.

Typically, the receptacle is provided with a vent 18 to permit gases to escape if pressure inside the receptacle rises to a sufficiently high degree.

An annular space is provided between the central rod and the receptacle walls and receives a reference electrode 19 which may be, for example, silver-chloride-coated silver wire. The space 20 in between is at least partially and preferably completely filled with a liquid mixture of electrolyte which may be introduced into the chamber through an aperture.

In polarographic measurements, two electrodes are commonly used, one of which is polarized and does not allow current to flow until depolarized by the substance being measured. In the cell structure, shown in FIG. 1, electrode 19 is the cathode and is polarized and frequently referred to as the reference electrode. The other electrode, electrode 14 as shown in FIG. 1, functions as an anode and is not polarized in the presence of the substance being measured and therefore will not restrict the flow of relatively large current and is frequently referred to as the sensor electrode. The electrodes shown in FIG. 1 are in an electrically insulating relation and the electrolyte material which occupies the chamber provides a conductive path between the two electrodes. Typical electrolytes include sodium or potassium chloride, buffers including carbonates, phosphates, bicarbonates, acetates, alkali or rare earth salts or other organic buffers or mixtures thereof may be used. The solvent for such an electrolyte may be water, glycols, glycerine and mixtures thereof as is well known in the art.

Figure 2:
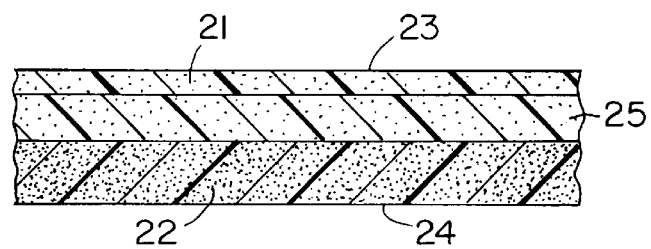
FIG. 2 is an enlarged view of a cross-section of one embodiment of the membrane of the present invention.

FIG. 2 shows a membrane in cross-sectional detail. The nonhomogeneous membrane has a thin, very dense layer 21, a less dense middle layer 25, and a thick, least dense or porous layer 22 which layers together form the composite structure. The enzyme shown symbolically by dots is dispersed uniformly in the thick portion or strata of the membrane. However, some of the enzyme may diffuse into the thin layer or middle layer during preparation of the membrane before the solvent for the cellulose acetate has evaporated. Membrane surface 24 is in electrical contact with the electrode. The membrane comprises the nonhomogeneous combination of the three layers and the enzyme, the outer free surface of which 23 represents the test surface which is to be brought into contact with the test sample to be analyzed.

In the preferred embodiment, the inner surface 24 which is an electrical contact with the electrode is about 65 microns in thickness, the middle layer is about 23 microns in thickness and has an average pore diameter of about 15 nanometers, and the outer layer in contact with the sample to be analyzed is about 2 microns. The overall thickness of the membrane is preferably about 90 microns.

The membrane of the invention may be produced by first casting an ultra thin, relatively dense cellulose acetate membrane onto a suitable surface and permitting it to dry. Then, the middle layer is cast directly on the thin layer. If the middle layer is omitted, the measurements may be more subject to nonlinearity due to oxygen depletion which is, in turn, caused by an increased flux of glucose molecules transported through the membrane and reacting with enzyme as sample concentration of glucose goes up. Then the thicker phase inversion type cellulose acetate membrane which is relatively porous may be cast directly on top of the middle membrane. It is possible to first cast the thick portion of the membrane and then cast the middle and then the thin portions directly on top of it.

The phase inversion member or more porous portion of the membrane composite is formed by providing a solution of cellulose acetate in an organic inert solvent such as acetone. The solution is then mixed with a nonsolvent for the cellulose acetate. Suitable nonsolvents include ethanol and water mixtures.

It is also desirable that the aqueous enzyme solution be introduced as a part of the nonsolvent phase.

The following specific example illustrates how the invention may be carried out but should not be considered as limiting thereof in any way.

EXAMPLE

On a clean glass plate, spread a solution formed of 2 g. of cellulose acetate in 40 ml. of acetone to a wet thickness of 0.1 mm. Air dry the layer.

On that dry layer, spread a solution of 4 g. of cellulose acetate in 40 ml. of acetone and 1.25 ml. of ethyl alcohol to a wet thickness of 0.30 mm. over the dry layer.

The inner layer solution is prepared by mixing 1.25 ml. of ethyl alcohol into a solution of 5 g. of cellulose acetate in 40 ml. of acetone. This is then placed in a salt water ice bath and stirred continuously. In 0.1 ml. increments, a total of 1.25 ml. of an aqueous glucose oxidase solution is then added to the polymer solution. Before mixing, the oxidase solution contains 2,000 to 3,000 International units of glucose oxidase per ml. Then, 0.25 ml. of a glutaraldehyde solution in water is added. The oxidase solution and the glutaraldehyde solution are added incrementally with continuous stirring over 10 to 15 minutes. The mixing is stopped and the material allowed to deaerate for 5 minutes.

The third membrane solution is then spread on top of the second membrane to a wet thickness of 0.2 mm. The spread film is then permitted to dry for several hours at room temperature. The membrane is then ready for use.

The enzyme preparation may simply be a mixture of the appropriate enzyme such as glucose oxidase in water. Of course, other materials such as a binder or cross-linking agent like glutaraldehyde may be included in the enzyme preparation. Likewise, the proportion of enzyme to water in the preparation is immaterial as long as a flowable paste or solution is formed which may be coated or pressed easily into the solution. Sufficient enzyme is incorporated into the solution to prepare an adequate reactive amount for measurement.

The membrane composite of the present invention is a self-supporting film of a total thickness which may range from about 50 to 130 microns, preferably about 90 microns. The composite membrane may be shaped to any particular configuration or size or may be cut or dimensioned in any particular way to fit receptacles for polarographic cells or electrodes of any suitable dimension. It may, in particular, be fastened to an O-ring for use in an electrode such as described in U.S. Pat. Nos. 4,092,233 or 4,415,666.

To fasten the membrane to a rubbery O-ring of an appropriate size, a gluing operation may be employed. The membrane may also be cast or dip coated directly onto an electrode surface.

In addition to cellulose acetate, other polymers capable of being dissolved in solvents and undergoing phase inversion with the addition of a weak solvent or nonsolvent would be potential membrane materials. Such polymers include cellulose nitrate, ethylcellulose and other cellulose derivatives. In addition, polycarbonate is a suitable alternative if methylene chloride is employed as a solvent instead of acetone or other ketones.

While the cellulose acetate membrane structure described above is preferred, it is possible to attenuate the glucose diffusion to the enzyme sites with a different membrane structure. Between the sample and the porous membrane containing the enzyme can be placed an ultra thin silicone membrane. The silicone membrane would be designed to reduce the diffusion coefficient of glucose so that, even at high sample concentrations (25 millimoles per liter) the glucose concentration at the enzyme does not overload the oxygen availability.

The silicone membrane would be designed to have 1 to 10 percent porosity and have a pore diameter of from 0.1 to 100 microns.

Figure 3:
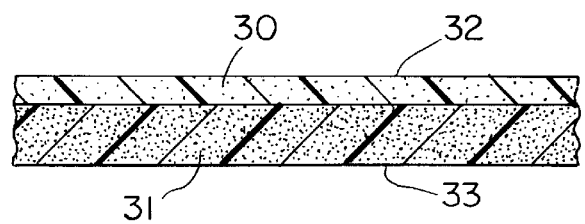
FIG. 3 is an enlarged view of a cross-section of another embodiment of the membrane of the present invention.

FIG. 3 shows this embodiment with the sample side silicone membrane 30 (with a sample-side surface 32) attached to the porous, enzyme filled layer 31 (with an electrode-side surface 33).

As a substitute or alternative for the lower chain alcohols present in the phase inversion mixture formamide can be used.

Once the sensor is prepared, it is applied to the task of determining the analyte concentration in a test sample by means of two operations which can be carried out in any order.

The measurement operation involves contacting the sample to the outside membrane surface or test surface 23. The electrical signal generated by the sensor in contact with the sample is related in magnitude to the concentration of the component (e.g., glucose) in the sample. Because the action of the enzyme and the exclusionary effect of the membrane keeps interfering components of the test sample from registering on the sensor; the sensor electrical signal is a function of the glucose concentration in the sample.

In prior art sensors, the function between concentration and the sensor signal was not linear over the biological range of the analyte (e.g. for glucose, 0 to 500 mg/dl).

Although the area of electrochemical sensors teaches many specific electrical signal values that can be monitored, the preferred signal in this application is the maximum voltage increase per unit time (mv/sec) between initial sample contact and steady state. This rate signal can be read, typically, in less than 20% of the time required to insure a steady state value.

If conventional glucose-loaded membranes are used, the rate signal is not linear with glucose sample concentration over the biological range of glucose concentration in an undiluted sample (0–500 mg/dl). The glucose resistance layer of the present invention decreases the diffusion coefficient of glucose to the enzyme to the extent that the function becomes linear over the biological range. In general, this will be achieved for the rate signal if the glucose resistance membrane is engineered so that its diffusion coefficient keeps the glucose concentration at the enzyme zone below the oxygen concentration in the zone, from time zero to a time passed the time of maximum voltage rate increase, for a sample concentration of 500 mg/dl.

The glucose diffusion coefficient of the resistance membrane can be adjusted to optimum by selection of membrane material, adjustment of porosity of the membrane, adjustment of range of effective pore size, and/or thickness of the membrane.

One difficulty with the sensor of the type described herein is that, when the sensor is calibrated using a glucose-water solution of a known concentration, the rate signal from the sensor equals the rate signal which would result from measuring an undiluted test sample having a glucose concentration of approximately twice the concentration of the calibrating solution. Put another way, the rate signal from undiluted test sample, e.g. blood, is about half of the rate signal from a calibrating solution of the same glucose concentration. While this anomaly can be rendered less; problematic in certain situations by various means, e.g., by high dilution of the blood sample (1 to 10) or by conversion factors, there are circumstances where 1-to-1 correspondence is preferred.

It has been discovered that the 1-to-1 correspondence between rate signals in glucose solutions and undiluted test sample, e.g. blood, can be achieved by adding an effective amount of the enzyme catalase to the calibrating solution.

When catalase is present in the calibrating solution at a level of 120 kU/ml, the rate signals are the same for calibrating solutions and undiluted test sample, e.g. blood, of the same glucose concentration.

While it is not entirely clear why catalase has this effect on the sensor reading, it is known that catalase is present is blood and in blood plasma (to different degrees), and that catalase can function to scavenge hydrogen peroxide by catalyzing the reaction of two molecules of hydrogen peroxide to one molecule of oxygen and two molecules of water.

How catalase in the calibrating sample would effect the sensor signal is less clear. Catalase is probably too large to diffuse through the membrane, so it would seem that it is not acting directly on the electrode area or even reaching the electrode area. Possibly, the concentration of hydrogen peroxide, which migrates into the calibrating solution from the enzyme zone, is being purged by the catalase in the calibrating solution. This must be in order for the calibrating solution to effect the sensor in the same way that blood effects the sensor.

Further variations and modifications of the invention, as will be apparent to those skilled in the art after reading the foregoing, are intended to be encompassed by the claims that are appended hereto.

We claim:

1. A three-layered contiguous membrane prepared by the method comprising:
   (a) providing a first solution comprising a first polymer dissolved in an inert organic solvent and casting said first solution onto a first inert support surface wherein said support is unreactive with said first polymer and said support does not form a bond to said first polymer,
   (b) permitting said first solution to form a 1 to 10 micron film and thereby obtaining a first layer,
   (c) providing a second polymer dissolved in a second inert organic solvent and mixing said second polymer with a nonsolvent for said second polymer to obtain a second solution,
   (d) casting a 0.30 mm wet thickness of said second solution onto said first layer, and thereafter permitting said second solution to dry to form a second layer having an average pore diameter of about 15 nanometers and a thickness ranging from 10 to 30 microns,
   (e) providing a third solution comprising a third polymer dissolved in a third inert organic solvent, mixing said third solution with a nonsolvent for said third polymer and with a water solution of glucose oxidase to obtain a dispersion and thereafter casting said dispersion onto said second layer, and thereafter permitting said third polymer to dry to form a 40 to 80 micron third layer, wherein said third layer is less dense than said first and second layers and said first layer is more dense than said second layer and wherein said layers of the membrane are fused together such that no clear distinction can be made between the layers at the boundary and the boundary between the layers is a diffusion zone and wherein said membrane has a thickness of from 50 to 130 microns.

2. The membrane according to claim 1 wherein said first layer has a thickness of from about 2 to about 5 microns and said second layer has a thickness of from about 15 to about 25 microns.

3. The membrane according to claim 1 wherein said second layer is about 23 microns in thickness and said first layer is about 2 microns in thickness and said third layer is about 65 microns in thickness.

4. The membrane according to claim 1 wherein said membrane has an overall thickness of about 90 microns and said second layer is about 23 microns in thickness.

5. The membrane according to claim 1 wherein said second layer is about 23 microns in thickness.

6. The membrane according to claim 5 wherein said first, second, and third inert organic solvents are the same and said first and second polymers are the same.

7. The membrane according to claim 1 wherein said first, second, and third inert organic solvent is a ketone.

8. The membrane according to claim 7 wherein said water solution of glucose oxidase further comprises ethanol.

9. A polarographic cell structure for use in a electrochemical analysis of an unknown, said cell comprising an electrically insulating receptacle; an electrode mounted in said receptacle, and a three-layered membrane, said membrane prepared by a method comprising:

(a) providing a first solution comprising a first polymer dissolved in an inert organic solvent and casting said first solution onto a first inert support surface wherein said support is unreactive with said first polymer and said support does not form a bond to said first polymer, (b) permitting said first solution to form a 1 to 10 micron film and thereby obtaining a first layer, (c) providing a second polymer dissolved in a second inert organic solvent and mixing said second polymer with a nonsolvent for said second polymer to obtain a second solution, (d) casting a 0.30 mm wet thickness of said second solution onto said first layer, and thereafter permitting said second solution to dry to form a second layer having an average pore diameter of about 15 nanometers and a thickness ranging from 10 to 30 microns, (e) providing a third solution comprising a third polymer dissolved in a third inert organic solvent, mixing said third solution with a nonsolvent for said third polymer and with a water solution of glucose oxidase to obtain a dispersion and thereafter casting said dispersion onto said second layer, and thereafter permitting said third polymer to dry to form a 40 to 80 micron third layer, wherein said third layer is less dense than said first and second layers and said first layer is more dense than said second layer and wherein said layers of the membrane are fused together such that no clear distinction can be made between the layers at the boundary and the boundary between the layers is a diffusion zone and wherein said membrane has a thickness of from 50 to 130 microns.

10. The polarographic cell structure according to claim 9 wherein in said membrane, said first layer has a thickness of from about 2 to about 5 microns and said second layer has a thickness of from about 15 to about 25 microns and said first and second polymers are the same and said first, second and third inert solvents are the same.

11. The polarographic cell structure according to claim 10 wherein in said membrane, said second layer is about 23 microns in thickness.

12. The polarographic cell structure according to claim 11 wherein in said membrane, said third layer is about 65 microns in thickness, and said first layer is about 2 microns and said overall thickness of said membrane is 90 microns.

13. A system for measuring glucose concentration in a test sample, said system comprising:

(a) a hydrogen peroxide electrode adapted to generate a signal, (b) the three-layered contiguous membrane as recited in claim 1, and (c) a calibrating solution comprising a known concentration of glucose and a hydrogen peroxide scavenger.

14. The system according to claim 13 wherein in (c) said hydrogen peroxide scavenger is catalase.

15. The system according to claim 14 wherein in (c) said catalase is present in an amount of about 120 kU/ml of said calibrating solution.

* * * * *